US00PP28375P3

(12) United States Plant Patent
Danziger

(10) Patent No.: US PP28,375 P3
(45) Date of Patent: Sep. 12, 2017

(54) ***LOBULARIA* PLANT NAMED 'DLOBRASTRM'**

(50) Latin Name: *Lobularia maritime*
Varietal Denomination: DLOBRASTRM

(71) Applicant: Gavriel Danziger, Moshav Mishmar Hashiva (IL)

(72) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 97 days.

(21) Appl. No.: 14/757,334

(22) Filed: Dec. 16, 2015

(65) Prior Publication Data

US 2017/0181349 P1 Jun. 22, 2017

(51) Int. Cl.
*A01H 5/02* (2006.01)

(52) U.S. Cl.
USPC ..... Plt./263.1

(58) Field of Classification Search
USPC ..... Plt./263.1
See application file for complete search history.

*Primary Examiner* — Anne Grunberg
(74) *Attorney, Agent, or Firm* — Cassandra Bright

(57) ABSTRACT

A new and distinct cultivar of *Lobularia* plant named 'DLOBRASTRM' is disclosed, characterized by long lasting dark red-purple flowers, compact, semi-trailing and freely branching plant form. Plants have a long flowering period. The new variety is a *Lobularia*, normally produced as an outdoor garden or container plant.

2 Drawing Sheets

Figure 1:
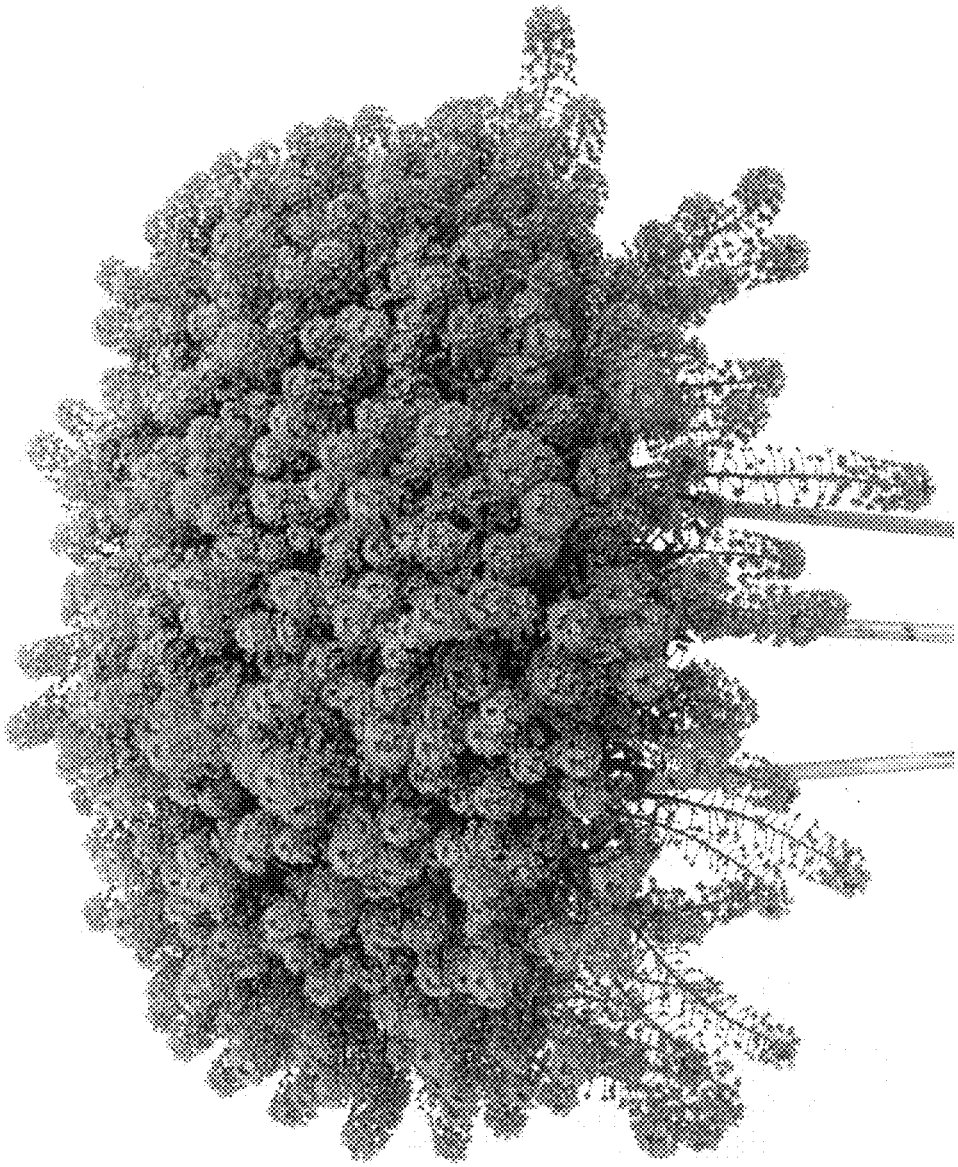

Latin name of the genus and species: *Lobularia maritime*.
Variety denomination: 'DLOBRASTRM'.

BACKGROUND OF THE INVENTION

The new *Lobularia* cultivar is a product of a planned breeding program conducted by the inventor, Gavriel Danziger, in Moshav Mishmar Hashiva, Israel. The objective of the breeding program was to produce new *Lobularia* varieties for ornamental commercial applications. The open pollination resulting in this new variety was made during March of 2012.

The seed parent is the proprietary variety referred to as *Lobularia* 'AY-13-558'. The pollen parent is unknown as it was an open pollination breeding program. The new variety was discovered in February of 2014 by the inventor in a group of seedlings resulting from the April 2013 crossing, in a research greenhouse in Moshav Mishmar Hashiva, Israel.

Asexual reproduction of the new cultivar was performed by vegetative cuttings. This was first performed at a research greenhouse in Moshav Mishmar Hashiva, Israel in February of 2014 and has shown that the unique features of this cultivar are stable and reproduced true to type in more than 10 successive generations.

SUMMARY OF THE INVENTION

The cultivar 'DLOBRASTRM' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DLOBRASTRM' These characteristics in combination distinguish 'DLOBRASTRM' as a new and distinct *Lobularia* cultivar:

1. Compact and semi-trailing habit
2. Long flowering period.
3. Free branching.
4. Dark red-purple flower color.

Plants of the new cultivar 'DLOBRASTRM' are similar to plants of the seed parent, *Lobularia* 'AY-13-558' in most horticultural characteristics, however, plants of the new cultivar 'DLOBRASTRM' differ in the following;

1. Plants of the new variety are bushier than plants of the female parent.
2. Plants of the new variety are more floriferous than plants of the female parent.
3. Plants of the new variety have better heat tolerance than plants of the female parent.
4. Plants of the new variety flower for a longer period than plants of the female parent.

COMMERCIAL COMPARISON

Plants of the new cultivar 'DLOBRASTRM' are comparable to the patented commercial variety *Lobularia* 'INLBUBLUPR'. U.S. Plant Pat. No. 24,516. The two *Lobularia* varieties are similar in most horticultural characteristics; however, the new variety 'DLOBRASTRM' differs in the following:

1. Plants of the new variety are more compact and dense than plants of 'INLBUBLUPR'.
2. Plants of the new variety are less cold sensitive than plants of 'INLBUBLUPR'.
3. Plants of the new variety have shorter and tighter inflorescences than plants of 'INLBUBLUPR'.
4. Plants of new variety have red-purple flowers; flowers of "INLBUBLUPR' are purple and white.

Plants of the new cultivar 'DLOBRASTRM' can also be comparable to the unpatented commercial variety *Lobularia* 'DLOBUBPINK', U.S. Plant Pat. No. 27,669. The two

*Lobularia* varieties are similar in most horticultural characteristics; however, the new variety 'DLOBRASTRM' differs in the following:

1. Plants of the new variety produce dark pink flowers; flowers of 'DLOBUPINK' are light pink.
2. Plants of new variety have a more compact and moderate trailing habit than plants of 'DLOBUPINK'.
3. Plants of new variety are less vigorous than plants of 'DLOBUPINK'.

BRIEF DESCRIPTION OF THE PHOTOGRAPHS

The accompanying photograph in FIG. 1 illustrates in full color a typical plant of 'DLOBRASTRM' grown in a greenhouse, in a 13 cm pot. Age of the plant photographed is approximately 8 weeks from an unrooted cutting.

Figure 2:
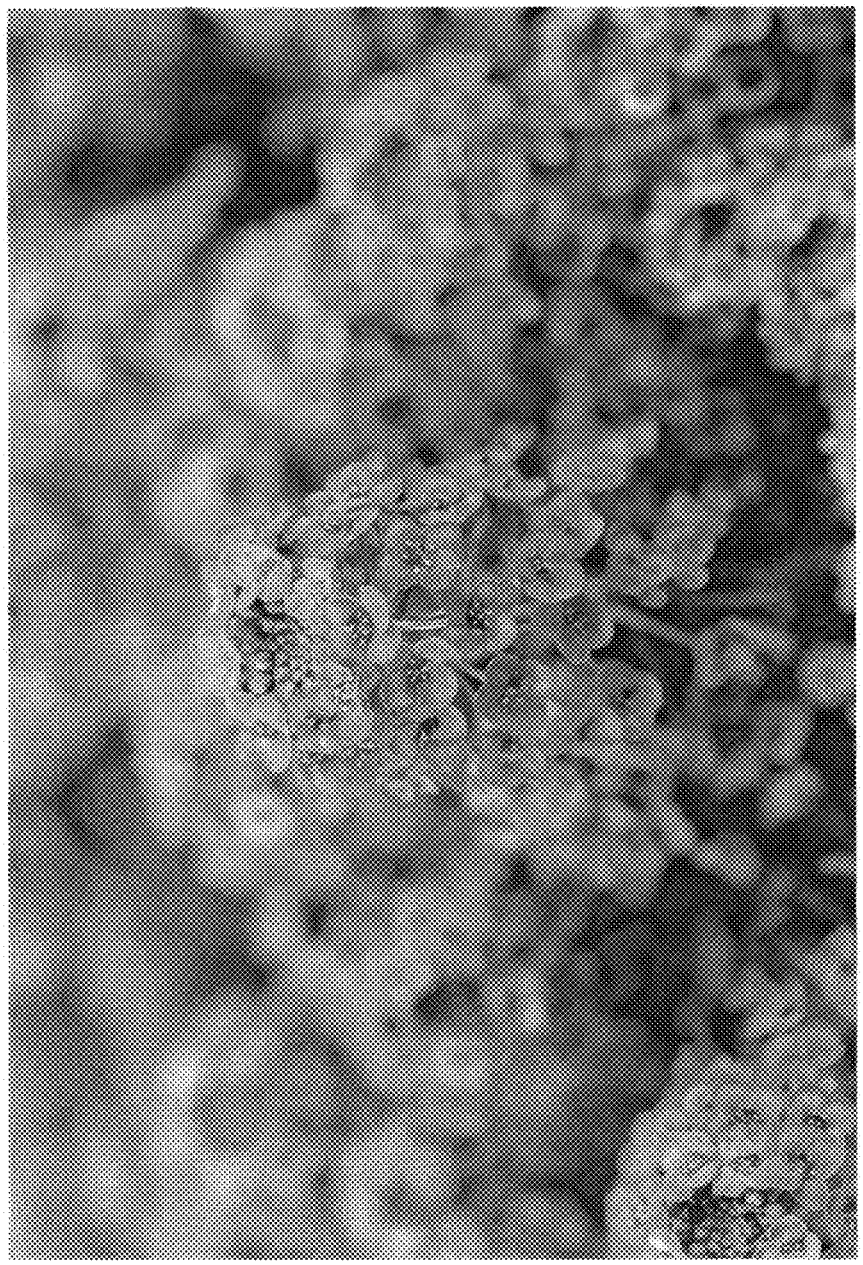

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2001 except where general terms of ordinary dictionary significance are used. The following observations and measurements describe 'DLOBRASTRM' plants grown in the Autumn, to Spring in moderate climate in a greenhouse, in Moshav Mishmar Hashiva, Israel. The growing temperature ranged from 16° C. to 30° C. during the day and from 9° C. to 16° C. during the night. This cultivar performs well at higher temperatures: up to 35° C. General light conditions are high light levels 60,000 to 90,000 Lux Measurements and numerical values represent averages of typical plant types.

Botanical classification: *Lobularia maritime* 'DLOBRASTRM'.

PROPAGATION

Type of propagation typically used: Cutting.
Time to initiate roots: 14 to 20 days at approximately 16° C.
Root description: Thin, fibrous, freely branching. Near RHS White 155C in color.

PLANT

Age of plant described: Approximately 10 weeks.
Container size of the plant described: 13 cm.
Growth habit: Compact semi-trailing.
Height: Approximately 14 cm.
Plant spread: Approximately 30 cm (radius).
Growth rate: Medium.
Branching characteristics: Freely Branching.
Approximate quantity of lateral branches: Approximately 5 to 6 primary lateral branches and numerous secondary and tertiary lateral branches.
Length of lateral branches: Approximately 27 cm.
Diameter of lateral branches: Approximately 0.3 to 0.4 cm.
Texture of lateral branches: Slightly Pubescent.
Lateral branch shape: Hexagonal in cross section.
Lateral branch strength: Strong.
Lateral branch color: Near RHS Yellow-green 144B.
Number of leaves per lateral branch: Average 24.

FOLIAGE

Leaf:
- *Arrangement*.—Alternate.
- *Shape of blade*.—Oblanceolate.
- *Average length*.—Approximately 4 to 4.5 cm. (Mature foliage — 5.0 to 6.0 cm).
- *Average width*.—Approximately 0.5 to 0.7 cm. (Mature foliage — 1.0 cm).
- *Apex*.—Acute.
- *Base*.—Cuneate.
- *Attachment*.—Sessile.
- *Margin*.—Entire.
- *Texture of top surface*.—Glabrous. Slightly Pubescent.
- *Texture of bottom surface*.—Glabrous. Slightly Pubescent.
- *Color*.—Young foliage upper side: Near RHS Yellow-Green 146B. Young foliage under side: Near RHS Yellow-Green 146B. Mature foliage upper side: Near RHS Yellow-Green 146B. Mature foliage under side: Near RHS Yellow-Green 146C.
- *Venation*.—Indistinguishable from foliage blade.
- *Petiole*.—Not present.

FLOWER

Bloom period:
- *Natural season*.—Long lasting flowering period. From March through December in Moshav Mishmar, Israel.
- *In commercial production, flowering begins from a rooted cutting*.—Approximately 6 to 8 weeks.

Inflorescence:
- *Arrangement*.—Panicle.
- *Height*.—Approximately 10 to 15 cm.
- *Width*.—Approximately 2.0 to 3.0 cm.
- *Quantity of flowers per inflorescence*.—Approximately 60 to 70 flowers.

Bud:
- *Bud shape*.—Globose spherical.
- *Bud length*.—Approximately 1.5 mm.
- *Bud diameter*.—Approximately 1.5 mm.
- *Bud color*.—Near RHS Yellow-Green 146B.
- *Rate of opening*.—Individual flowers: Fully open approximately 2 to 3 days from the bud stage.

Individual flower:
- *Type of individual flowers*.—Single flower.
- *Shape*.—Cross Shaped.
- *Quantity of flowers and buds per plant*.—Approximately 60 to 70 flowers and buds per inflorescence — more than 2500 flowers per plant.
- *Diameter of entire flower*.—Approximately 0.5 to 0.6 cm.
- *Depth of flower*.—Less than 1 mm.
- *Flower longevity on plant*.—Approximately 6 to 7 days.
- *Persistent or self-cleaning*.—Self-cleaning.
- *Fragrance*.—Sweet, honey like.

Petals:
- *Length of petal*.—Approximately 3 mm.
- *Width of petal*.—Approximately 2.5 mm.
- *Apex*.—Rounded.
- *Base*.—Reniform.

*Shape of petal*.—Oval.
*Petal margin*.—Entire.
*Petal arrangement*.—4 petals fused in a single whorl.
*Petal number*.—4 petals.
*Petal appearance*.—Matte.
*Petal texture*.—Smooth, glabrous.

Color:
*Upper surface at first opening*.—Near RHS Red-Purple 71B.
*Upper surface at maturity*.—Near RHS Red-Purple 71C.
*Upper surface at fading*.—Near RHS Red-Purple 72D.
*Under surface at first opening*.—Near RHS Red-Purple 71B.
*Under surface at maturity*.—Near RHS Red-Purple 71B.
*Under surface at fading*.—Near RHS Red-Purple 72C.

Sepal:
*Number*.—4.
*Sepal appearance*.—4 sepals.
*Sepal arrangement*.—4 sepals in a single whorl.
*Sepal length*.—Approximately 1 mm.
*Sepal width*.—Approximately 0.5 mm.
*Sepal shape*.—Elliptic.
*Base*.—Truncate.
*Apex shape*.—Acute.
*Margin*.—Entire.
*Color*.—Near RHS Yellow-Green 146B.

Peduncle:
*Length*.—Approximately 2.0 to 3.0 cm.
*Diameter*.—Approximately 2 mm.
*Angle*.—Not relevant.
*Strength*.—Strong.
*Color*.—Near RHS Yellow-green 144A.

Pedicel:
*Length*.—Approximately 0.8 cm.
*Diameter*.—Approximately 0.6 mm.
*Angle*.—Approximately 80-90 degrees.
*Strength*.—Flexible, moderately strong.
*Color*.—Near RHS Yellow-green 146B.

REPRODUCTIVE ORGANS

Number of pistils per flower: 1.
Pistil length: Approximately 1.2 mm.
Stigma shape: Rounded to broadly spreading.
Stigma color: Near RHS Yellow-Green 144C.
Style color: Near RHS Green 143C.
Style length: Approximately 0.5 mm.
Ovary color: Near RHS Yellow-Green 144A.
Stamens quantity: 6.
Stamen length: 1.5 mm.
Anther shape: Elliptic.
Anther size: Less than 0.5 mm.
Anther color: Near RHS Yellow 7B.
Pollen color: Near RHS Yellow 7A.
Pollen quantity: Abundant.

OTHER CHARACTERISTICS

Disease resistance: Neither resistance nor susceptibility to common diseases and pests of *Lobularia* has been observed. Typical diseases include *Rhizoctonia solani* and *Peronospora*. A common pest is *Macrosteles quadrilineatus*.

Environmental tolerance: Plants of the new *Lobularia* have been noted to have good tolerance for temperatures from 1° C. to 38° C. Plants are also tolerant of rain and minor drought.

Fruits and seeds: The fruits and seeds are elliptical and flat. The color of the mature seed is near RHS Greyed-Orange 165B. Minute, dust-like, immeasurable.

What is claimed is:

1. A new and distinct cultivar of *Lobularia* plant named 'DLOBRASTRM' as herein illustrated and described.

* * * * *